United States Patent [19]

Takahama et al.

[11] 4,224,280

[45] Sep. 23, 1980

[54] CARBON MONOXIDE DETECTING DEVICE

[75] Inventors: Teizo Takahama; Toyoki Kazama, both of Kawasaki, Japan

[73] Assignee: Fuji Electric Co., Ltd., Kawasaki, Japan

[21] Appl. No.: 924,324

[22] Filed: Jul. 13, 1978

[30] Foreign Application Priority Data

Jul. 18, 1977 [JP] Japan .................................. 52-85917
Jul. 18, 1977 [JP] Japan .................................. 52-85918

[51] Int. Cl.² .......................................... G01N 27/04
[52] U.S. Cl. .......................................... 422/98; 73/23; 338/34
[58] Field of Search ................ 23/232 E; 422/94, 98; 338/34; 73/23, 27 R; 324/65 R, 71 SN

[56] References Cited

U.S. PATENT DOCUMENTS

| | | | |
|---|---|---|---|
| 3,479,257 | 11/1969 | Shaver | 23/232 E X |
| 3,901,067 | 8/1975 | Boardman, Jr. et al. | 338/34 X |
| 4,030,340 | 6/1977 | Chang | 422/98 X |
| 4,066,413 | 1/1978 | Segawa et al. | 422/98 |

Primary Examiner—Arnold Turk

Attorney, Agent, or Firm—Sughrue, Rothwell, Mion, Zinn and Macpeak

[57] ABSTRACT

A carbon monoxide detecting device which exhibits a stepwise change in film current over a preselected range in carbon monoxide concentration is disclosed.

According to the present invention, in one embodiment, a first film predominantly of stannic oxide ($SnO_2$) is formed on an insulating layer, and a second film predominantly of platinum (Pt) is formed on said first film. The second film is of an average film thickness of about 0.3 to 30 platinum atom layers. In another embodiment, gold (Au) is incorporated into said second film, and the second film is of an average film thickness of about 0.3 to 30 platinum atoms and the amount of gold ranges up to 50 atomic percent of the amount of platinum. In a third embodiment, a donor selected from the group consisting of antimony (Sb) and bismuth (Bi) is incorporated into the first film, and an intermediate film predominantly of stannic oxide ($SnO_2$) having an acceptor selected from the group consisting of platinum (Pt), aluminum (Al), and boron (B) is formed intermediate said first and second films. The first, intermediate, and second films are formed, for example, by a high frequency reactive sputtering method.

10 Claims, 17 Drawing Figures

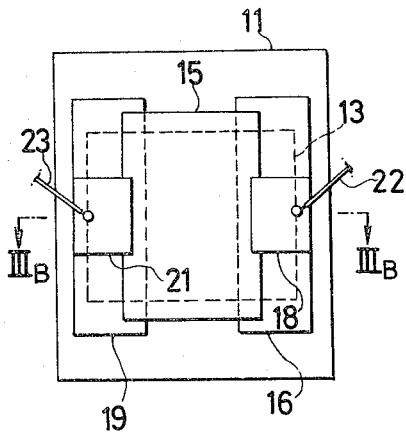
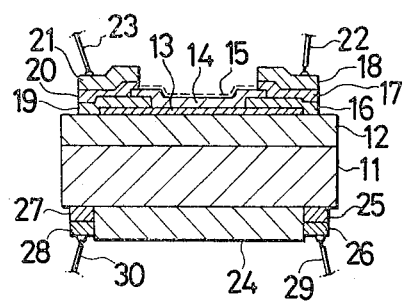
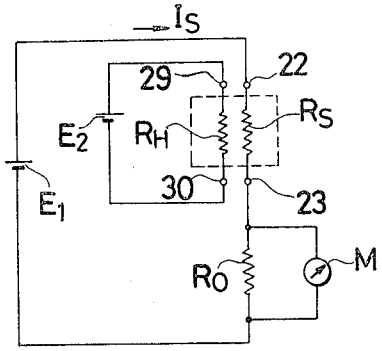

CARBON MONOXIDE DETECTING DEVICE

BACKGROUND OF THE INVENTION

This invention relates to a carbon monoxide detecting device having a plurality of semiconductor films.

With respect to conventional gas detecting devices which utilize semiconductor films, a hydrogen or reductive gas detecting device has been proposed, for example, by U.S. Pat. No. 3,479,257.

The detecting device disclosed in U.S. Pat. No. 3,479,257 is shown in FIGS. 1A and 1B. In the detecting device, a pair of electrodes 2 and 3 are provided on a first surface of a substrate 1, while a film 4 of conductive material employed as a resistance for heating is deposited on the opposite surface of the substrate 1 by vacuum evaporation. A metal oxide film 5 is formed between the electrodes 2 and 3, and an activation catalyst 6 is deposited in the form of minute islands on the film 5 by vacuum evaporation. The electrodes 2 and 3 are connected to lead wires 7 and 8, respectively.

The film 5 is a metal oxide selected from the group consisting of tungsten (W), molybdenum (Mo), chromium (Cr), niobium (Nb), nickel (Ni), iron (Fe) and titanium (Ti) or their compounds.

The catalyst 6 is a metal selected from the group consisting of platinum (Pt), iridium (Ir), rhodium (Rh), gold (Au) and palladium (Pd) or their mixtures.

FIG. 2 is a graph plotting in a log/log manner film current in mA on the vertical axis versus hydrogen concentration in PPM on the horizontal axis of the gas detecting device constructed in accordance with the description presented above. As is apparent from FIG. 2, as the hydrogen concentration is increased, the film current I of the metal oxide film is monotonously and gradually increased. In general, a gas detecting device is provided with a warning device which is activated when the detected gas concentration reaches, for instance, 100-300 PPM. Because the film current I is monotonously increased, the rate of change of current I with respect to the rate of change of the detected hydrogen concentration is low in the conventional gas detecting device, and therefore, the setting of the film current to operate the warning device is rather difficult. In addition, the above described patent disclosure is silent as to the sensitivity of the conventional gas detecting device for detection of carbon monoxide.

When a burner is operating in the incomplete combustion state, the burner generates carbon monoxide (CO), but also generates nitrogen oxides ($NO_x$). However, according to experiments performed by the inventors, the detection characteristic of the conventional gas detecting device is affected by the nitrogen oxides. Specifically, the output characteristic of the carbon monoxide detecting device, having a film current characteristic which monotonously increases, is lowered by the nitrogen oxides. Therefore, because of the nitrogen oxides, it is very difficult to detect carbon monoxide alone with the carbon monoxide detecting device.

SUMMARY OF THE INVENTION

It is an object of the present invention to provide a carbon monoxide detecting device having a readily obtainable stepwise variation in film current over a selected carbon monoxide concentration range.

It is a further object of the present invention to provide a carbon monoxide detecting device having a detection characteristic that is substantially unaffected by other coexisting gases, such as nitrogen oxides, present in the gas atmosphere being sensed.

The foregoing objects are achieved by the carbon monoxide detecting device of the present invention. According to the present invention, in one embodiment, a first film predominantly of stannic oxide ($SnO_2$) is formed on an insulating layer, and a second film predominantly of platinum (Pt) is formed on said first film. The second film is of an average film thickness of about 0.3 to 30 platinum atom layers. In another embodiment, gold (Au) is added into said second film, and the second film is of an average film thickness of about 0.3 to 30 platinum atom layers and the amount of gold ranges up to 50 atomic percent of the amount of platinum. In another embodiment, a donor selected from the group consisting of antimony (Sb) and bismuth (Bi) is added into first film, and an intermediate film predominantly of stannic oxide ($SnO_2$) having an acceptor selected from the group consisting of platinum (Pt), aluminum (Al), and boron (B) is formed intermediate said first and second films. The first, intermediate, and second films are formed, for example, by a high frequency reactive sputtering method. The detecting devices according to these embodiments exhibit a stepwise change in film current over a preselected range in carbon monoxide concentration, and, thus, are very suitable for use with a warning device.

BRIEF DESCRIPTION OF THE DRAWINGS

FIG. 3A shows a top plan view of a carbon monoxide detecting device according to the present invention;

FIG. 3B shows a cross-sectional view of the carbon monoxide detecting device according to the present invention taken along line $III_B$—$III_B$ in FIG. 3A;

FIG. 4 shows a schematic circuit diagram of an experimental circuit utilizing the carbon monoxide detecting device of the present invention;

DETAILED DESCRIPTION OF THE PREFERRED EMBODIMENTS

Figure 1B:
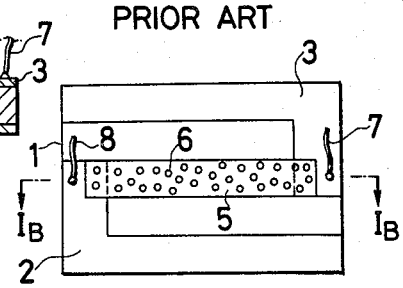
FIG. 1B shows a cross-sectional view of the conventional gas detecting device taken along line $I_B$—$I_B$ in FIG. 1A.
Figure 1A:
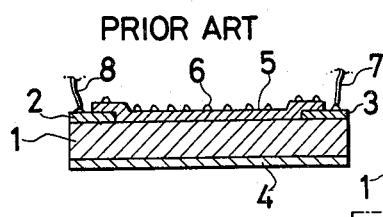
FIG. 1A shows a top plan view of a conventional gas detecting device.
Figure 2:
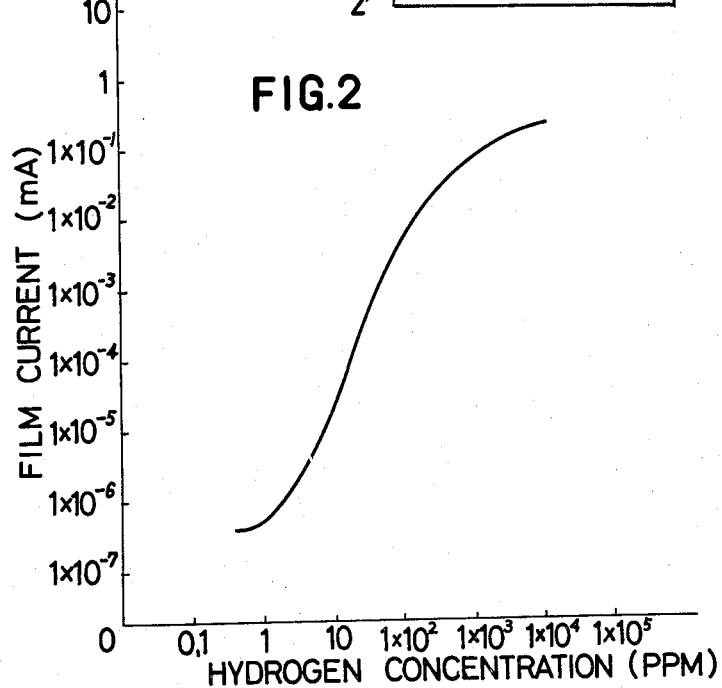
FIG. 2 is a graph plotting film current $I_S$ on the vertical axis versus hydrogen concentration on the horizontal axis of the characteristic curve of the conventional gas detecting device of FIGS. 1A and 1B.

The first embodiment of the present invention will be described with reference to FIGS. 3A and 3B. Reference numeral 11 designates a substrate made of, for example, silicon (Si). An insulating film 12 of silicon oxide (SiO$_2$) is formed on a first surface of substrate 11. A first film 13 is formed on the insulating film 12. First film 13 predominantly comprises stannic oxide, and has a donor selected from the group consisting of antimony (Sb) and bismuth (Bi). A second film 15 predominantly of platinum is formed on the first film 13. An intermediate film 14 is formed intermediate the first film 13 and second film 15. The intermediate film 14 predominantly comprises stannic oxide and has an acceptor selected from the group consisting of platinum, aluminum and boron. The films 13, 14 and 15 are formed, for example, in accordance with a high frequency reactive sputtering method. In forming each of the films 13 and 14, a target is made of tin, and a plurality of minute, thin pieces of antimony or platinum are placed on the target. The second film 15 is so formed on the intermediate film 14 that the second film 15 is of an average thickness of 0.3 to 30 platinum atom layers and does not exhibit a metallic, electrical conductivity because of the small thickness, as is well known in the art.

In the second embodiment of the present invention, which is obtained by modifying the second film 15 of the abovedescribed first embodiment, the modified second film 15 comprises platinum (Pt) and has gold (Au) incorporated therein. In this embodiment, the modified second film 15 is also formed, for example, in accordance with a high frequency sputtering method, and the target is made of platinum. A plurality of minute, thin pieces of gold are placed on the target. The amount of platinum of the modified third layer is of an average film thickness of 0.3 to 30 platinum atom layers, and the amount of gold is ranges up to 50 atm percent of the amount of platinum. The modified second film is formed so that it does not exhibit a metallic, electrical conductivity, because of the small thickness, as is well known in the art. In addition, the modified second film 15 can be formed by preparing the target with platinum containing gold of a suitable concentration level, and by subjecting the target to sputtering.

In addition, in the above-described first and second embodiments, a pair of first electrodes 16 and 19 are formed on the insulating film 12. A pair of respective electrodes 16 and 19 is interposed between the first film 13 and the intermediate film 14. A pair of second electrodes 17 and 20 are provided on first electrodes 16 and 19, respectively, and a part of each second electrode overlaps film 14. Films 18 and 21 of gold are formed on electrodes 17 and 20 to connect lead wires 22 and 23 to the electrodes 17 and 20, respectively.

Substrate 11 serves both as substrate and as a heating resistor for heating the carbon monoxide detecting device. For this second purpose, heating electrodes 25 and 27 are provided on the second surface of the substrate 11, and are connected to heating lead wires 29 and 30 through films 26 and 28 of gold, respectively. A film 24 is provided between heating electrodes 25 and 27 and acts as an insulating surface protecting the film in a manner similar to that of film 12. It should be noted, however, that film 24 may be omitted.

The thickness of various elements in the first and second embodiments, as shown in FIGS. 3A and 3B, are given by way of example, in Table 1 below.

TABLE 1

| | |
|---|---|
| Substrate 11 | 200 $\mu m$ |
| Insulating Layer 12 | 0.7 $\mu m$ |
| First Film 13 | 0.06 $\mu m$ |
| Intermediate Film 14 | 0.07–0.15 $\mu m$ |
| Second Film 15 (unmodified and modified) | Average 0.0001–0.012 $\mu m$ |
| First Electrodes 16, 19 | 0.2 $\mu m$ |
| Second Electrodes 17, 20 | 0.2 $\mu m$ |

Shown in FIG. 4 is an experimental circuit which utilizes the various embodiments of the carbon monoxide detecting device of the present invention. In this circuit, reference character $E_1$ designates a driving power supply for operating the carbon monoxide detecting device. The voltage of the power supply $E_1$ is, for example, approximately 1 V. The driving power supply $E_1$ is connected to lead wires 22 and 23 through a current detecting resistor $R_0$. A heating power supply $E_2$ is provided to heat the carbon monoxide detecting device, and its voltage is set, for example, to about 4 V. The heating power supply $E_2$ is connected to the lead wires 29 and 30. The resistor $R_0$ is a fixed resistor of, for example, 1 ohm, and a volt meter M is connected in parallel between the two terminals of resistor $R_0$. Reference character $R_S$ designates the resistance of the films between lead wires 22 and 23. Reference character $I_S$ designates a film current flowing in that film. Reference character $R_H$ designates a heating resistance between lead wires 29 and 30. In the experimental result described below, the film resistance $R_S$, and the film current $I_S$ were calculated using the voltage readings obtained on voltmeter M. It should be noted that the heating temperature of the substrate 11 can be varied by varying the voltage provided by power supply $E_2$.

Figure 5:
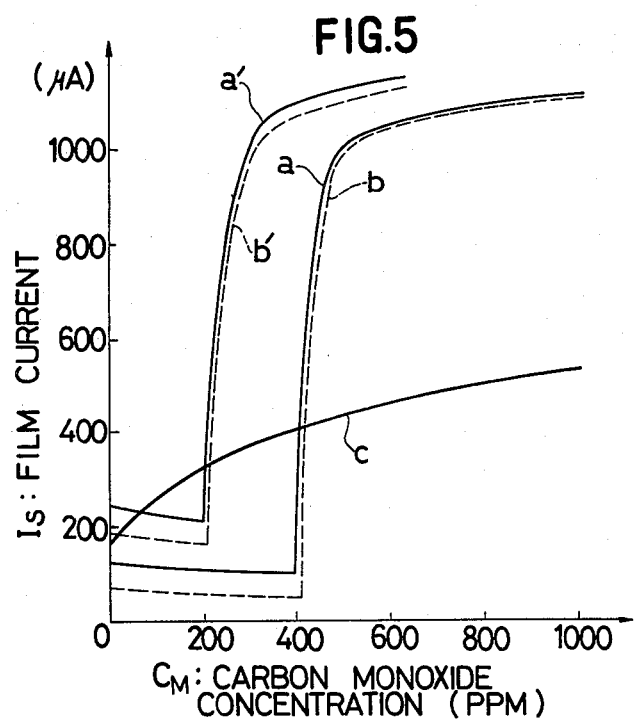
FIG. 5 is a graph, plotting film current in $\mu A$ on the vertical axis versus carbon monoxide (CO) concentration in PPM on the horizontal axis, of the characteristic curves produced by the first and second experiments employing carbon monoxide detecting devices on the present invention.

FIG. 5 is a graph representation of the first and second experiments. FIG. 5 plots film current $I_S$ in $\mu A$ on the vertical axis versus carbon monoxide concentration $C_M$ in PPM on the horizontal axis detected by the carbon monoxide detecting device of the present invention employed in the experimental circuit shown in FIG. 4. In the first and second experiments, the ambient temperature was 25° C., the ambient humidity was 60%, and the substrate 11, first film 13 and intermediate film 14 were heated to about 210° C. The characteristic curve a was generated by the first embodiment of the present invention by varying the carbon monoxide concentration $C_M$. As is apparent from characteristic curve a, the film current $I_S$ is substantially equal to the film current produced when the CO concentration is zero when the carbon monoxide concentration $C_M$ is less than about 400 ppm, and is increased in a stepwise fashion when the carbon monoxide concentration $C_M$ is in the range of from about 400 to 500 ppm, and is substantially constant when the carbon monoxide concentration $C_M$ is higher than about 500 PPM.

The characteristic curve a' of FIG. 5 was generated by the second embodiment of the present invention by varying the carbon monoxide concentration $C_M$. As is apparent from characteristic curve a', the film current $I_S$ is substantially equal to the film current produced when the CO concentration is zero when the carbon monoxide concentration $C_M$ is less than about 200 PPM, and is increased in a stepwise fashion when the carbon monoxide concentration $C_M$ is in the range of from about 200 to 300 PPM, and is substantially constant when the carbon monoxide concentration $C_M$ is higher than about 300 PPM.

Accordingly, in both the first and second embodiments, a carbon monoxide detecting device is obtained which exhibits an abrupt stepwise increase in film current $I_S$ when the carbon monoxide concentration is in a certain concentration range. In addition, it is now apparent that the base current of the film current $I_S$ and the stepwise concentration range can be changed by changing the quantity of antimony added to second film 15 and by changing the thickness of first film 13.

The characteristic curve b of FIG. 5 represents the film current $I_S$ characteristic produced by the first embodiment when the carbon monoxide concentration $C_M$ was changed by the further addition of nitrogen oxides ($NO_x$) in a concentration of 20 PPM. Furthermore, the characteristic curve b' in FIG. 5 represents the film current $I_S$ characteristic produced by the second embodiment when the carbon monoxide concentration $C_M$ was changed by the further addition of nitrogen oxides in a concentration of 20 PPM. According to these characteristic curves b and b', it is very apparent that the carbon monoxide detection produced by the first and the second embodiments of the present invention was scarcely affected by the introduction of nitrogen oxides into the gas atmosphere being sensed.

In order to investigate the effects produced by the second film 15, a second experiment was performed by using a carbon monoxide detecting device, as shown in FIGS. 3A and 3B, from which the second film 15 was removed. The results of the second experiment are plotted by a characteristic curve c in FIG. 5. It is apparent from characteristic curve c that removal of the second film 15 consisting of platinum, or platinum and gold, from either the first or the second embodiment causes the film current $I_S$ not to exhibit the stepwise film current $I_S$ variation.

According to another experiment (not shown in the FIGS.), it has been discovered that even if the average atom layer of platinum forming second film 15 is varied in the range between 0.3 to 30 platinum atom layers, the concentration range for carbon monoxide detection where the film current $I_S$ is increased in a stepwise manner is substantially unaffected by the change in thickness of second film 15. The inventors are uncertain as to the technical explanation of why the film current increases in a stepwise fashion over a certain carbon monoxide concentration range, as shown in FIG. 5, for the first and second embodiments having second film 15 of platinum or platinum and gold formed on films 13 and 14.

In the third experiment, the quantity of gold in second film 15 was varied while the quantity of platinum was maintained constant. In the third experiment, the quantity of gold with respect to the quantity of platinum was defined by an area ratio. The term "gold area ratio" was defined as the percentage of the total area of thin pieces of gold with respect to the whole area of a target of platinum used to fabricate second film 15 in accordance with the high frequency sputtering method.

Figure 6:
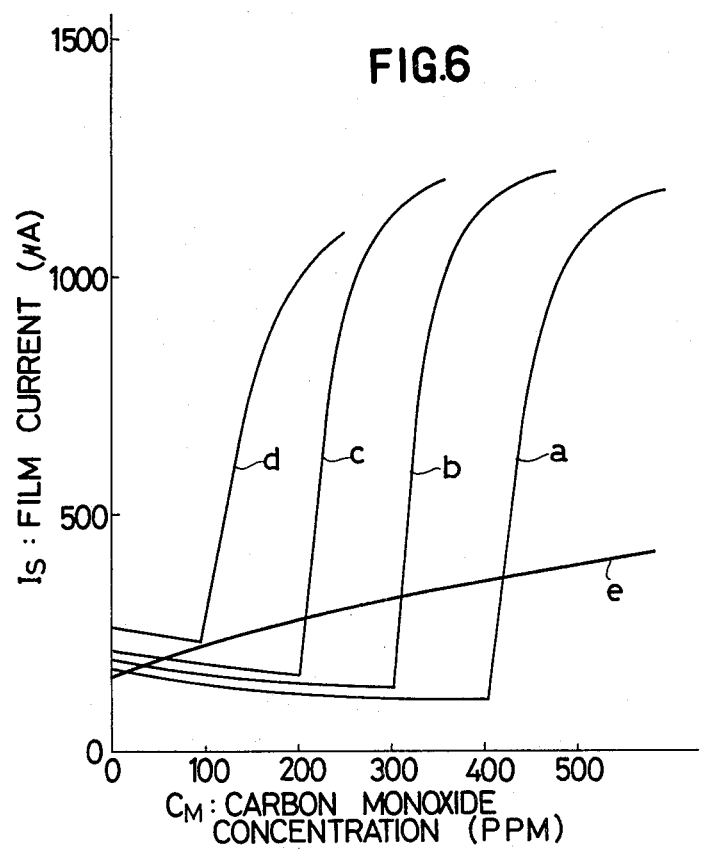
FIG. 6 is a graph, plotting film current in $\mu A$ on the vertical axis versus carbon monoxide (CO) concentration in PPM on the horizontal axis, of the characteristic curves produced by the third experiment employing carbon monoxide detecting devices of the present invention.

FIG. 6 is a graph representation of the third experiment. FIG. 6 plots film current $I_S$ in $\mu A$ on the vertical axis versus carbon monoxide concentration $C_M$ in PPM on the horizontal axis detected by carbon monoxide detecting devices of the present invention having different gold area ratios for film 15. The ambient temperature, the ambient humidity, and the temperature of substrate 11, first film 13 and intermediate film 14 were maintained constant in the third experiment.

The characteristic curves a, b, c and d in FIG. 6 represent experiment results for gold area ratios of 0%, 3.3%, 5% and 9.3%, respectively. It is apparent from these characteristic curves a, b, c and d that as the quantity of gold is increased, the range of carbon monoxide concentration $C_M$ in which film current $I_S$ varies in a stepwise manner is shifted toward the low $C_M$ zone. It is also apparent that the range of carbon monoxide variation which produces the stepwise variation is also reduced.

According to additional experiments performed by the inventors, it has been discovered that the film current $I_S$ makes a stepwise variation that can be electronically sensed, with a gold area ratio of up to about 50%. In addition, it is also discovered that if the platinum average atom layers are varied in a range of 0.3 to 30, the carbon monoxide concentration $C_M$ range in which film current $I_S$ varies stepwise is substantially unaffected.

In addition, a carbon monoxide detecting device having a second film 15 made only of gold, i.e. the gold area ratio being 100%, was tested. These tests generated the characteristic curve e shown in FIG. 5. As is apparent from characteristic curve e, the film current $I_S$ does not exhibit the stepwise variation. It should be noted that the inventors are not in agreement as to the theoretical explanation for the stepwise film current $I_S$ produced by carbon monoxide detecting devices of the present invention having a second film 15 of platinum or, platinum and gold, formed on first and intermediate films 13, 14, respectively.

Figure 7A:
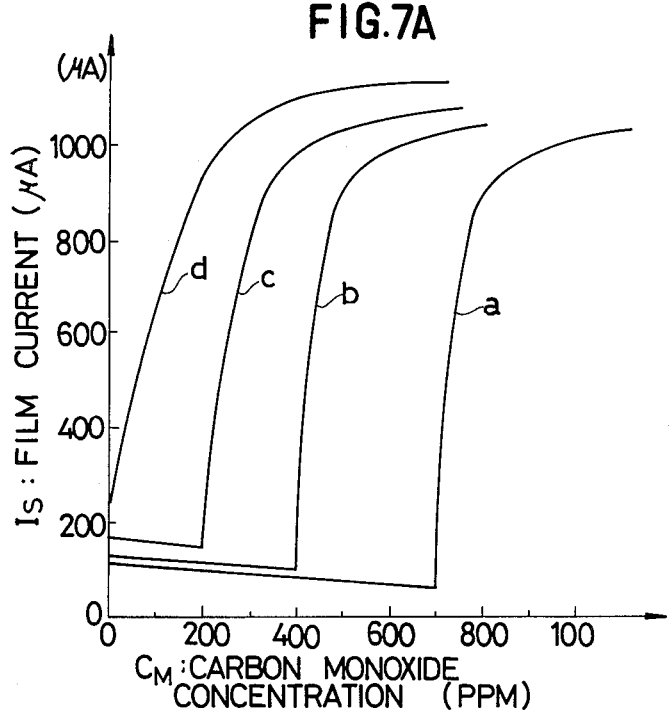
FIG. 7A is a graph, plotting film current in $\mu A$ on the vertical axis versus carbon monoxide (CO) concentration in PPM on the horizontal axis, of the characteristic curves produced by the fourth experiments employing the first embodiment of the carbon monoxide detecting device of the present invention.

FIG. 7A is a graph representation plotting the characteristic curves generated by the fourth experiments in which the effect of heating temperature of the device was investigated using the first embodiment of the present invention. FIG. 7A plots film current $I_S$ in $\mu$A on the vertical axis versus carbon monoxide concentration $C_M$ is PPM on the horizontal axis. In FIG. 7A, temperature was employed as the varied parameter. The characteristic curves a, b, c, and d plot carbon monoxide concentration $C_M$ versus film current $I_S$ at heating temperatures T of 225° C., 210° C., 185° C. and 150° C., respectively. In the experiments, the ambient temperature was about 25° C. and the ambient humidity was about 60%. It is apparent from FIG. 7A that the carbon monoxide concentration $C_M$ range which produces the stepwise change in the film current $I_S$ is changed in accordance with the heating temperature T, and is increased as the heating temperature T is increased. However, it should be noted that the film current $I_S$ did not exhibit the stepwise variation when the heating temperature T of the carbon monoxide detecting device of the first embodiment was lower than about 150° C.

Figure 7B:
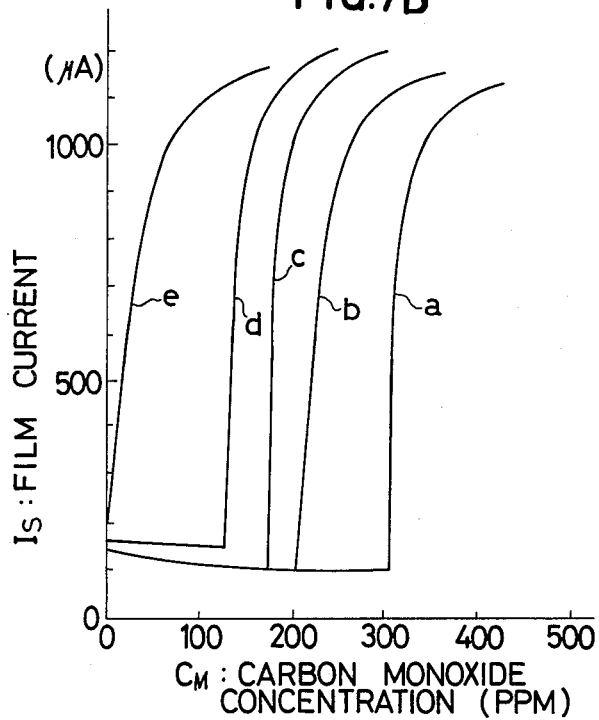
FIG. 7B is a graph, plotting film current in $\mu A$ on the vertical axis versus carbon monoxide (CO) concentration in PPM on the horizontal axis, of the characteristic curves produced by the fourth experiments employing the second embodiment of the carbon monoxide detecting device of the present invention.

FIG. 7B is a graph representation plotting the generated by the fourth experiments in which the effect of heating temperature of the device was investigated using the second embodiment of the present invention. FIG. 7B plots film current $I_S$ is $\mu$A on the vertical axis versus carbon monoxide concentration $C_M$ in PPM on the horizontal axis. In FIG. 7B, temperature was employed as the varied parameter. The characteristic curves a, b, c, d and e plot carbon monoxide concentration $C_M$ versus film current $I_S$ characteristic curves at heating temperatures T of 220° C., 210° C., 200° C., 190° C. and 170° C., respectively. In the experiments, the ambient temperature was about 25° C., and the ambient humidity was about 60%. It is apparent from FIG. 7B that the carbon monoxide concentration $C_M$ range which produces the stepwise change in the film current $I_S$ is changed in accordance with the heating temperature T, and is increased as the heating temperature T is increased. However, it should be noted that the film current $I_S$ did not exhibit the the stepwise variation when the heating temperature of the carbon monoxide detecting device of the second embodiment was lower than about 170° C.

Figure 8:
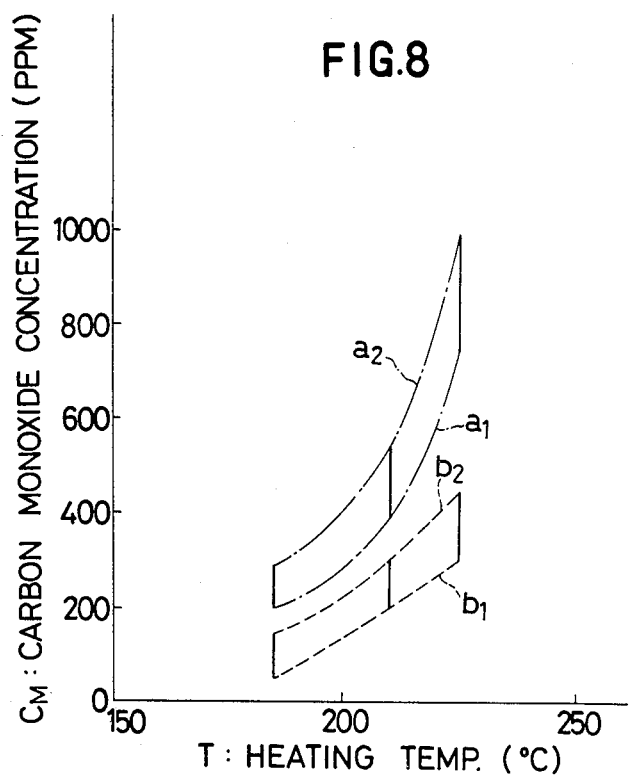
FIG. 8 is a graph representation of the fifth experiments plotting, for devices according to the first and second embodiments, the ranges of carbon monoxide concentration $C_M$ on the vertical axis which produce the stepwise variation in film current, with the heating temperature T represented on the horizontal axis.

FIG. 8 is a graph representation of the fifth experiment plotting, for devices according to the first and second embodiments, the ranges of carbon monoxide concentrations $C_M$ which produce the stepwise variation in film current or film resistance. FIG. 8 plots carbon monoxide concentration $C_M$ in PPM on the vertical axis versus heating temperature T on the horizontal axis. Characteristic curves a-1 and a-2 were generated using a plurality of detecting devices whose films 15 were made only of platinum, and which were subjected to heating temperatures of 185° C., 210° C. and 225° C. Fluctuation of the devices was taken into consideration. Characteristic curves b-1 and b-2 were generated using a plurality of detecting devices whose films 15 were formed with a gold area ratio of 5%, and which were subjected to heating temperatures of 185° C., 210° C. and 225° C. Fluctuation of the devices was taken into consideration. It is now apparent that the stepwise ranges plotted in FIGS. 7A and 7B fall between the characteristic curves a-1 and a-2 or b-1 and b-2, respectively.

The characteristic curves a-1 and a-2 are now compared with characteristic curves b-1 and b-2. When the heating temperature T is changed by an amount of 40° C., that is, from 185° C. to 225° C., in the characteristic curves a-1 and a-2, the carbon monoxide concentration $C_M$ for varying the film current or the film resistance stepwise is changed by about 600 PPM, that is, from about 250 ppm to about 850 PPM, while in the characteristic curves b-1 and b-2, the concentration $C_M$ is changed only by an amount of 250 PPM, that is, from about 100 ppm to about 350 PPM. Thus, it is now apparent that if the second film 15 is made of both platinum and gold instead of only platinum, the temperature dependability of the carbon monoxide concentration $C_M$ for varying, in a stepwise manner, the film current or resistance is improved.

The results of the sixth experiments in which the relationship between the amounts of antimony (Sb) added to the first film 13 and the stepwise variations of the film current $I_S$ or the film resistance are now presented. In the experiments, the amount of antimony added to first film 13 was varied in the range of 0–20% area ratio with respect to tin used to form the target for the sputter method. However, it was discovered that the film current $I_S$ or the film resistance stepwise variation produced by the carbon monoxide concentration was substantially unaffected by the addition of antimony to first film 13. The term "area ratio of antimony with respect to tin" is intended to mean that, where a number of pieces of antimoney are placed on a target of tin and a first film 13 is formed by the high frequency reactive sputtering method, the area occupied by the antimony with respect to the whole area of the target of tin is expressed as a percentage.

The results of the seventh experiments in which the relationship between the amounts of platinum (Pt) in the intermediate film 14 and the film current $I_S$ or resistance are now presented. The seventh experiments were performed under the conditions shown in Table 1. It should be noted that the heating temperature of the substrate was 210° C. for each of the experiments in Table 1.

TABLE 1

| Experiment | First Film 13 | | Second Film 14 | | Third Film 15 | |
| | Sb area ratio | Thickness | Pt area ratio | Thickness | Au area ratio | Average thickness |
| --- | --- | --- | --- | --- | --- | --- |
| A-1 | 4% | 0.06$\mu$m | 4.6% | 0.06$\mu$m | — | 0.0003$\mu$m |
| A-2 | 4% | 0.06$\mu$m | 4.6% | 0.06$\mu$m | 5% | 0.0003$\mu$m |
| B-1 | 4% | 0.06$\mu$m | 1.6% | 0.06$\mu$m | — | 0.0003$\mu$m |
| B-2 | 4% | 0.06$\mu$m | 1.6% | 0.06$\mu$m | 5% | 0.0003$\mu$m |
| C-1 | 4% | 0.06$\mu$m | — | — | — | 0.0003$\mu$m |
| C-2 | 4% | 0.06$\mu$m | — | — | 5% | 0.0003$\mu$m |

In Table 1, the term "Sb area ratio" is intended to mean the ratio of the area occupied by antimony with respect to the whole area of the target of tin, as was described above. Similarly, the term "Pt area ratio" is intended to mean, in the case where a number of thin pieces of platinum are placed on a target of tin and a film 14 is formed in accordance with the high frequency reactive sputtering method, the area occupied by the platinum with respect to the whole area of the target as expressed in a percentage form.

In Table 1, experiments A-1, B-1, and C-1 were performed using the first embodiment of the present invention, while experiments A-2, B-2 and C-2 were performed using the second embodiment.

Figure 9:
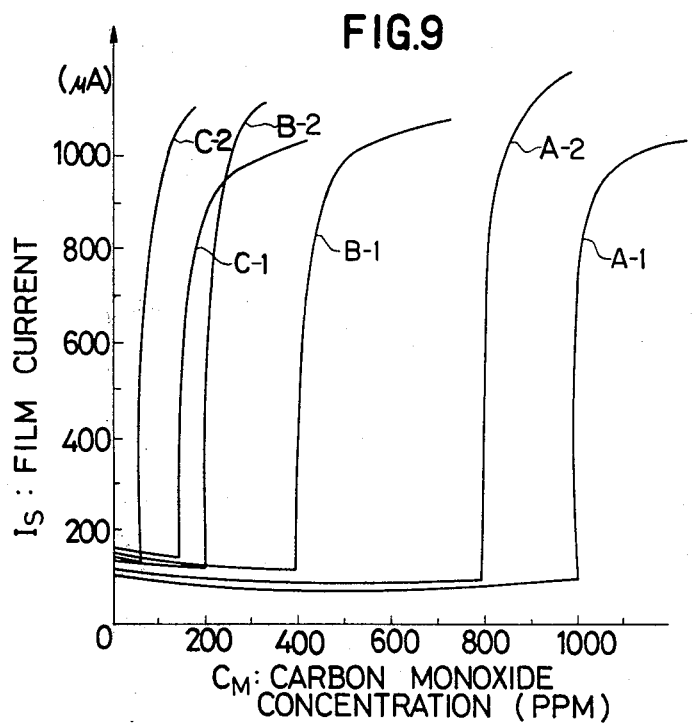
FIG. 9 is a graph representation plotting the characteristic curves produced by the seventh experiments performed under the conditions shown in Table 1.

FIG. 9 is a graph representation plotting the characteristic curves produced by the seventh experiments performed under the conditions shown in Table 1. FIG. 9 plots film current $I_S$ in $\mu A$ on the vertical axis versus carbon monoxide concentration $C_M$ in PPM on the horizontal axis. Reference characters in Table 1 are identical to those employed in FIG. 9. As is apparent from FIG. 9, as the platinum area ratio in intermediate film 14 is decreased, the carbon monoxide concentration $C_M$ which results in the film current $I_S$ exhibiting the stepwise variation is decreased. It should be noted well that characteristic curves C-1 and C-2 in FIG. 9 show that the film current $I_S$ stepwise variation can be obtained without the use of the film 14.

Figure 10A:
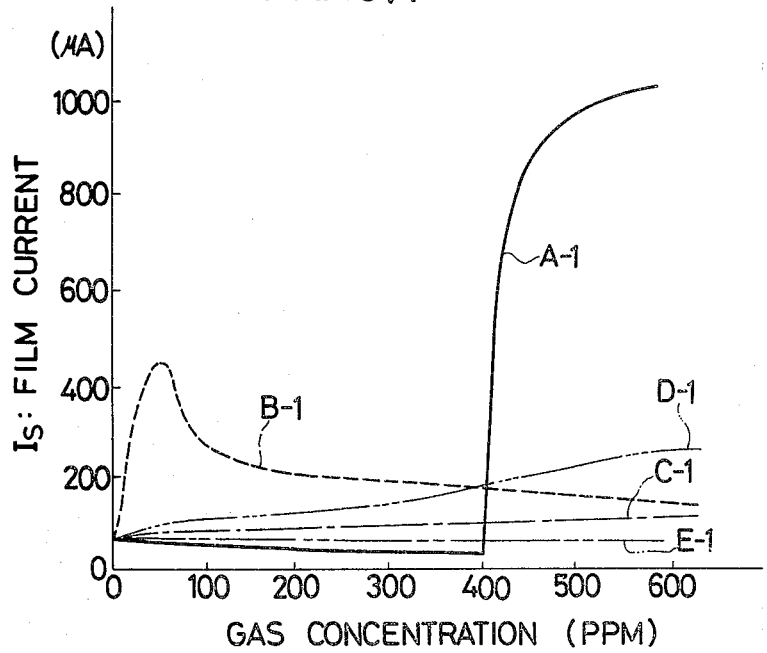
FIG. 10A is a graph representation, with the vertical axis being film current $I_S$ in $\mu A$ and the horizontal axis being carbon monoxide concentration $C_M$, plotting the characteristic curves generated by the eighth experiments in which the effects of various gases on the carbon monoxide detection response of the first embodiment of the present invention were investigated.
Figure 10B:
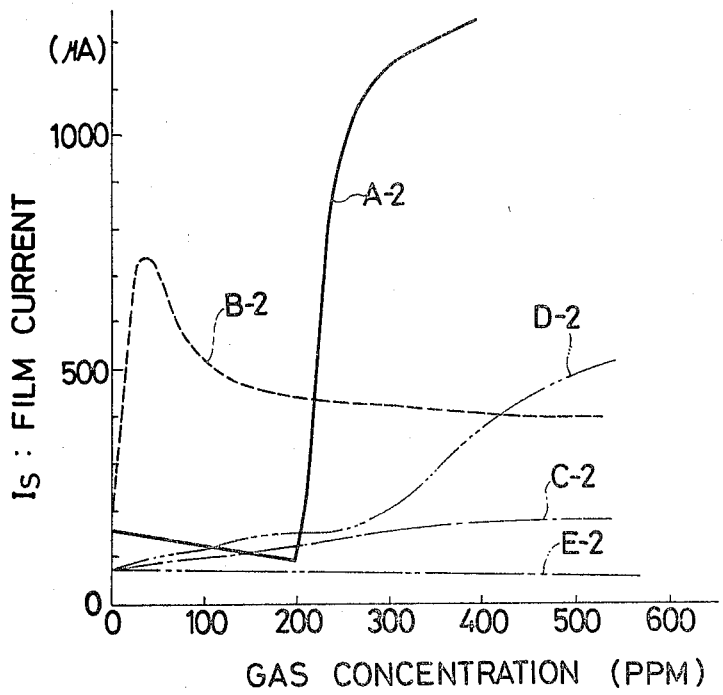
FIG. 10B is a graph representation, with the vertical axis being film current $I_S$ in $\mu A$ and the horizontal axis being carbon monoxide concentration $C_M$, plotting the characteristic curves generated by the eighth experiments in which effects of various gases on the carbon monoxide detection response of the second embodiment of the present invention were investigated.

FIGS. 10A and 10B are graph representation plotting the characteristic curves generated by the eighth experiments in which the effects of various gases on the carbon monoxide detection response were investigated. FIGS. 10A and 10B each plot film current $I_S$ in $\mu A$ on the vertical axis versus carbon monoxide concentration $C_M$ on the horizontal axis. The first embodiment of the present invention was used to generate FIG. 10A, and the second embodiment was used to generate FIG. 10B.

The heating temperature of the substrate 11 was about 210° C. in both FIGS. 10A and 10B. The characteristic curves A-1, B-1, C-1, D-1 and E-1 shown in FIG. 10A and the characteristic curves A-2, B-2, C-2, D-2 and E-2 shown in FIG. 10B plot the effect on the film currents $I_S$ caused by the gases of carbon monoxide (CO), ethylalcohol ($C_2H_5OH$), hydrogen ($H_2$), ethylene ($C_2H_4$), and methane ($CH_4$) or isobutane (iso-$C_4H_{10}$), respectively. As is apparent from FIGS. 10A and 10B, with the first and second embodiments of the detecting device of the present invention, the film current $I_S$ stepwise variation is significant when carbon monoxide is the gas atmosphere being sensed, but is practically insignificant when ethylalcohol, ethylene, hydrogen, methane, or isobutane is the gas atmosphere being sensed.

Figure 11:
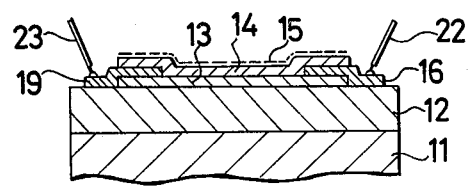
FIG. 11 is a cross-sectional side view of the third embodiment of the carbon monoxide detecting device of the present invention.

FIG. 11 is a cross-sectional side view showing a third embodiment of the present invention. In the third embodiment, the second electrodes 17 and 20 and the films 18 and 21, as shown in FIG. 3, are removed, and lead wires 22 and 23 are connected directly to electrodes 16 and 19, respectively. For the third embodiment, the various above-mentioned experiments using the experimental circuit shown in FIG. 4 were performed. The experiments confirm that the firm currents $I_S$ or the film resistance stepwise variation is produced by the third embodiment in a certain range of carbon monoxide concentration.

In addition, various experiments were conducted with the above-mentioned first, second and third embodiments having the second film 14 removed. These experiments also confirmed that the film current $I_S$ or the film resistance stepwise variation is produced in a certain range of carbon monoxide concentration.

Figure 12A:
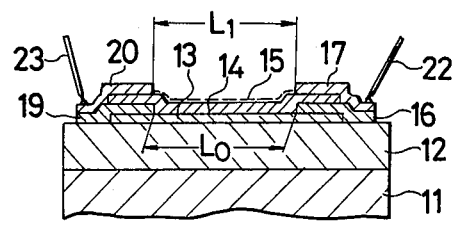
FIGS. 12A and 12B are cross-sectional side views of the fourth and fifth embodiments, respectively, of the carbon monoxide detecting device of the present invention.
Figure 12B:
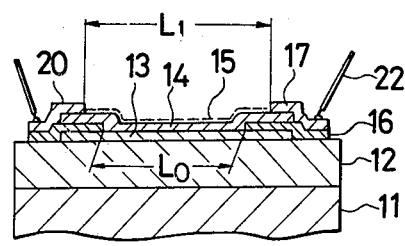

FIGS. 12A and 12B are cross-sectional side views showing the structures of the fourth and fifth embodiments, respectively, of the present invention. In the fourth embodiment, as shown in FIG. 12A, the distance $L_0$ between the first electrodes 16, 19 is made equal to the distance $L_1$ between the second electrodes 17, 20. In the fifth embodiment, as shown in FIG. 12B, the distance $L_0$ between the first electrodes 16, 19 is made smaller than the distance $L_1$ between the second electrodes 17, 20.

In the fourth and fifth embodiments, in the case when where the electrode thicknesses film thickness were made identical to those in the first or second embodiment, as shown in FIG. 3, respectively, experiments were performed for a carbon monoxide (CO) gas atmosphere, and for a gas atmosphere of carbon monoxide and nitrogen oxide ($NO_x$). The results of these experiments are indicated in Table 2 below.

TABLE 2

| Atmosphric gas | Film current $I_S$ ($\mu A$) | | |
|---|---|---|---|
| Experiment | Pure air | CO: 300 ppm | CO: 300 ppm NO: 10 ppm |
| (A) $L_0$: 0.7 mm $L_1$: 0.7 mm | 5.06 | 508 | 408 |
| (B) $L_0$: 0.7 mm $L_1$: 1.1 mm | 3.25 | 450 | 446 |

As is apparent from Table 2, in the case of the fourth embodiment where the distance $L_0$ is equal to the distance $L_1$, interference produced by nitrogen oxide is significant. Such nitrogen oxide interference is not desirable. One possible explanation for the difference in characteristics shown in Table 2 is that the difference is caused by impurities mixed during the formation of the electrodes.

As is apparent from the above description, in the present invention, a film of platinum or platinum and gold, having an atomic thickness that is narrow enough that the film does not show a metallic, electrical conductivity, is formed on a film which essentially contains stannic oxide. Therefore, according to the present invention, a carbon monoxide detecting device can be fabricated which produces a stepwise variation in film current $I_S$ when the concentration of carbon monoxide reaches a certain value. Thus, according to the present invention, a warning device can be utilized in a simple and accurate manner that senses when the film current or resistance varies stepwise. Furthermore, it should be noted that the detecting device according to the present invention is substantially unaffected by co-existing gases in the gas atmosphere being sensed, and exhibits improved temperature dependance characteristics.

What is claimed is:

1. A detector for a carbon monoxide gas comprising:
   (a) an insulating substrate;
   (b) a first film predominantly of stannic oxide ($SnO_2$) formed on said insulating substrate, and wherein a donor selected from the group consisting of antimony and bismuth is incorporated into said first film;
   (c) a second film predominantly of platinum formed on said first film; and
   (d) a film intermediate said first and second film, said intermediate film predominantly comprising stannic oxide and having an acceptor selected from the group consisting of platinum, aluminum, and boron.

2. A detector as recited in claim 1, wherein said second film has an average thickness in the range between 0.3 to 30 platinum atom layers.

3. A detector as recited in claim 1, wherein a pair of first electrodes are provided on said insulating substrate in such a manner that a part of each said electrode is interposed between said first and said intermediate films.

4. A detector as recited in claim 3, wherein a pair of second electrodes are electrically connected to said pair of first electrodes, respectively, and a part of each said second electrode overlaps said intermediate film.

5. A detector as recited in claim 4, wherein the distance between said pair of second electrodes is larger than the distance between said pair of first electrodes.

6. A detector for a carbon monoxide gas comprising:
(a) an insulating substrate;
(b) a first film predominantly of stannic oxide ($SnO_2$) formed on said insulating substrate, and wherein a donor selected from the group consisting of antimony and bismuth is incorporated into said first film;
(c) a second film formed on said first film, said second film comprising platinum and having gold incorporated therein, and
(d) a film intermediate said first and second film, said intermediate film predominantly comprising stannic oxide and having an acceptor selected from the group consisting of platinum, aluminum, and boron.

7. A detector as recited in claim 6, wherein the average thickness of said platinum in said second film is in the range of from 0.3 to 30 platinum atom layers, and said amount of gold added to said second layer ranges up to 50 atomic percent of the amount of said platinum in said second layer.

8. A detector as recited in claim 6, wherein a pair of first electrodes are provided on said insulating substrate in such a manner that a part of each said electrode is interposed between said first and said intermediate films.

9. A detector as recited in claim 8, wherein a pair of second electrodes are electrically connected to said pair of first electrodes, respectively, and a part of each said second electrode overlaps said intermediate film.

10. A detector as recited in claim 9, wherein the distance between said pair of second electrodes is larger than the distance between said pair of first electrodes.

* * * * *